(12) United States Patent
Flores et al.

(10) Patent No.: US 7,247,865 B2
(45) Date of Patent: Jul. 24, 2007

(54) SYSTEM AND METHOD OF DETECTING, NEUTRALIZING, AND CONTAINING SUSPECTED CONTAMINATED ARTICLES

(75) Inventors: Juan E. Flores, Owasso, OK (US); Charles E. Davis, Claremore, OK (US)

(73) Assignee: Lockheed Martin Corporation, Bethesda, MD (US)

( * ) Notice: Subject to any disclaimer, the term of this patent is extended or adjusted under 35 U.S.C. 154(b) by 489 days.

(21) Appl. No.: 10/335,501

(22) Filed: Dec. 31, 2002

(65) Prior Publication Data
US 2003/0136920 A1   Jul. 24, 2003

Related U.S. Application Data

(60) Provisional application No. 60/344,843, filed on Dec. 31, 2001.

(51) Int. Cl.
*G21K 5/10* (2006.01)
*G01N 21/17* (2006.01)

(52) U.S. Cl. .............. 250/455.11; 250/492.3; 378/69; 422/22

(58) Field of Classification Search ............ None
See application file for complete search history.

(56) References Cited

U.S. PATENT DOCUMENTS

| | | | |
|---|---|---|---|
| 2,609,928 A | 9/1952 | Doust | 209/111 |
| 3,592,326 A | 7/1971 | Zimmerle et al. | 198/33 R |
| 3,995,741 A | 12/1976 | Henderson | 209/111.5 |
| 4,494,655 A | 1/1985 | Horii et al. | 209/569 |
| 4,601,396 A | 7/1986 | Pavie | 209/569 |
| 4,627,540 A * | 12/1986 | Takeda | 209/555 |
| 4,769,551 A | 9/1988 | Hamashima et al. | 250/548 |
| 4,877,964 A | 10/1989 | Tanaka et al. | 250/455.1 |
| 4,918,315 A | 4/1990 | Gomberg et al. | 250/390.04 |
| 5,147,031 A | 9/1992 | Carpenter | 198/750 |

(Continued)

FOREIGN PATENT DOCUMENTS

WO    WO 83/00972    3/1983

OTHER PUBLICATIONS

U.S. Appl. No. 60/344,843, filed Dec. 31, 2001, entitled System and Method of Detecting, Neutralizing, and Containing Suspected Contaminated Articles. Applicant: Steven E. Flores.

(Continued)

*Primary Examiner*—Jack I. Berman
(74) *Attorney, Agent, or Firm*—Burns & Levinson LLP; Jacob N. Erlich; Orlando Lopez

(57) ABSTRACT

A comprehensive system and method of rendering the mail safe for handling and for detecting and containing suspect pieces and which can be fitted or retrofitted into mail and package processing facilities with relative ease. The system of the present invention includes a mail tray initial neutralizing sub-system, a subsequent neutralizing sub-system, an analyzing (potentially hazardous material detection) sub-system, a diverting mechanism, and a receiving and holding sub-system (secure out-sort pocket). All components can be controlled or operate in conjunction with a processing/computing sub-system. A feeder sub-system provides the mail from trays, after initial neutralization by the initial neutralizing sub-system, to the mail transport system.

26 Claims, 10 Drawing Sheets

U.S. PATENT DOCUMENTS

| | | | |
|---|---|---|---|
| 5,337,581 A | 8/1994 | Lott .............................. 62/264 |
| 5,386,482 A | 1/1995 | Basso et al. .................... 382/9 |
| 5,401,973 A * | 3/1995 | McKeown et al. ...... 250/492.3 |
| 5,424,547 A | 6/1995 | Stark et al. ................. 250/372 |
| 5,434,045 A | 7/1995 | Jost ............................... 435/1 |
| 5,606,169 A | 2/1997 | Hiller et al. ............ 250/455.11 |
| 5,700,426 A | 12/1997 | Schmitthaeusler et al. .... 422/29 |
| 5,719,678 A | 2/1998 | Reynolds et al. ........... 356/379 |
| 5,830,419 A * | 11/1998 | Held et al. .................. 422/307 |
| 5,917,925 A | 6/1999 | Moore ........................ 382/101 |
| 5,958,336 A | 9/1999 | Duarte ........................ 422/24 |
| 5,994,706 A * | 11/1999 | Allen et al. ............ 250/454.11 |
| 6,000,555 A | 12/1999 | Anma ........................ 209/534 |
| 6,014,450 A | 1/2000 | Heilper et al. .............. 382/101 |
| 6,071,440 A | 6/2000 | Wang et al. .................. 264/1.1 |
| 6,135,292 A | 10/2000 | Pettner ....................... 209/603 |
| 6,171,548 B1 | 1/2001 | Rose et al. ................... 422/20 |
| 6,228,330 B1 | 5/2001 | Herrmann et al. ..... 422/186.05 |
| 6,289,109 B1 | 9/2001 | Gocht et al. ................ 382/101 |
| 6,320,933 B1 | 11/2001 | Grodzins et al. ............. 378/89 |
| 6,426,507 B1 * | 7/2002 | Rangwalla et al. ...... 250/492.3 |
| 6,707,049 B1 * | 3/2004 | Lyons et al. ........... 250/453.11 |
| 6,742,703 B2 | 6/2004 | Esakov et al. |
| 2003/0145664 A1 * | 8/2003 | Schwarz et al. ......... 73/863.22 |
| 2003/0222132 A1 | 12/2003 | Esakov et al. |

OTHER PUBLICATIONS

M. Wolf et al., "Fast Address Block Location in Handwritten and Printed Mail-piece Images", Proc. of the Fourth Intl. Conf. on Document Analysis and Recognition, vol. 2, pp. 753-757, Aug. 18-20, 1997.

P.W. Palumbo et al., "Postal Address Block Location in Real Time", Computer, vol. 25, No. 7, pp. 34-42, Jul. 1992.

Partial International Search Report dated Jul. 15, 2004 for PCT/US02/41840. Applicant: Lockheed Martin Cooperation.

U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

* cited by examiner

SYSTEM AND METHOD OF DETECTING, NEUTRALIZING, AND CONTAINING SUSPECTED CONTAMINATED ARTICLES

CROSS REFERENCE TO RELATED APPLICATIONS

This application claims priority of U.S. Provisional Application No. 60/344,843 filed on Dec. 31, 2001, which is hereby incorporated by reference.

BACKGROUND OF THE INVENTION

This invention relates generally to the containment and detection of hazardous material in a mail sorting facility, and, more particularly to the detection, neutralization, and generating an alarm signal notifying others of contamination occurring as a result of objects such as mail being transported over a transport system.

Recently there has been increased awareness of the potential for large-scale introduction of hazardous materials, that is, either explosives or biological organisms to create chaos or to harm an intended set of victims. One potential delivery method that terrorists or other criminals utilize to deliver such hazardous materials is through the mail or other form of a delivery. In so doing damage, not only is damage incurred by the intended victims, but also to any set of potential victims that may be in a position of handling such objects as the mail during the delivery or distribution process.

Biological agents being purposely mailed may pose hazards to postal workers and the population at large. The biological agents can escape from envelopes during processing and leave dangerous residues on the exteriors of envelopes and packages, and may also contaminate the trays or tubs that are used to carry such pieces.

Currently, one solution available is to irradiate entire cages of mail at one time. However, the expense of irradiating all of the nation's mail can be prohibitive. A fast, comprehensive, effective and inexpensive method is required.

There currently is a need for a comprehensive system and method of rendering the mail safe for handling and for detecting and containing suspect pieces. In addition, there is a need for systems that can be fitted or retrofitted into mail and package processing facilities with relative ease. Furthermore there is a need for a method for automatically warning if biological agents are present in the mail being processed.

SUMMARY OF THE INVENTION

A comprehensive system and method of rendering the mail safe for handling and for detecting and containing suspect pieces and which can be fitted or retrofitted into mail and package processing facilities with relative ease are disclosed.

The system of the present invention includes a mail tray initial neutralizing sub-system, a subsequent neutralizing sub-system, a analyzing (potentially hazardous material detection) sub-system, a diverting mechanism, and a receiving and holding sub-system (secure out-sort pocket). All components can be controlled or operate in conjunction with a processing/computing sub-system. A feeder sub-system provides the mail from trays, after initial neutralization by the initial neutralizing sub-system, to the mail transport system. Although the system is shown with the three above-mentioned components, it should be noted that alternative systems can be configured with more components or fewer components depending on system specifications. Therefore, three components are shown for illustration purposes and should not be considered a limitation to the invention.

The process of initial neutralizing the mail items is initiated by receiving of an incoming tray, the mail items being disposed inside the incoming tray. The mail items in the incoming tray are exposed to neutralizing radiation while the incoming tray is being agitated to provide a uniform coverage of the surfaces of the mail items. In one embodiment, the contents of the incoming tray are then transferred to a receiving tray. The mail items in the receiving tray are exposed to neutralizing radiation while the receiving tray is being agitated to provide an even more uniform coverage of the irradiated surfaces. The receiving tray is conveyed out of the initial neutralizing sub-system to a feeder sub-system. The feeder sub-system provides the mail items from the receiving tray to a transport system.

The transport system provides the mail items to the analyzing sub-system. The analyzing sub-system obtains, while the mail items are being transported by the transport system, an indication of whether a mail item contains potentially hazardous materials. One embodiment of the analyzing sub-system uses intense backlighting techniques and an electronic imaging system and algorithm that looks for "Mounds" and "Speckles" within pieces. These Mounds and Speckles may indicate that a powder-like substance is within a mail item.

If a longer transport path and/or physical buffers are present in the transport sub-system, or if the time to analyze is increased or other techniques improve the analysis time required, other sources, such as X-rays, laser sources, and detection techniques, such as handwriting analysis, techniques for detecting hazardous materials, may be utilized.

The transport system provides the mail item from the analyzing sub-system to the neutralizer in order to expose the outer surfaces of the mail item to neutralizing radiation.

If the analyzing sub-system indicates that a mail item contains potentially hazardous materials, the mail item is diverted from the transport stream. The diverted mail item is isolated in a receiving and holding sub-system (secure out-sort pocket). An alarm can be generated as the mail item is diverted to the secure out-sort pocket. The secure out-sort pocket can include a neutralizing radiation source. Others can be alerted upon receiving the alarm. The secure out-sort pocket can be removed.

While the above sequence of operations describes an embodiment of the present invention, other sequences of operations are also within the scope of this invention.

For a better understanding of the present invention, together with other and further objects thereof, reference is made to the accompanying drawings and detailed description and its scope will be pointed out in the appended claims.

DETAILED DESCRIPTION OF THE PREFERRED EMBODIMENTS

A comprehensive system and method of rendering the mail safe for handling and for detecting and containing suspect pieces that can be fitted or retrofitted into mail and package processing facilities with relative ease are disclosed hereinbelow.

Figure 1:
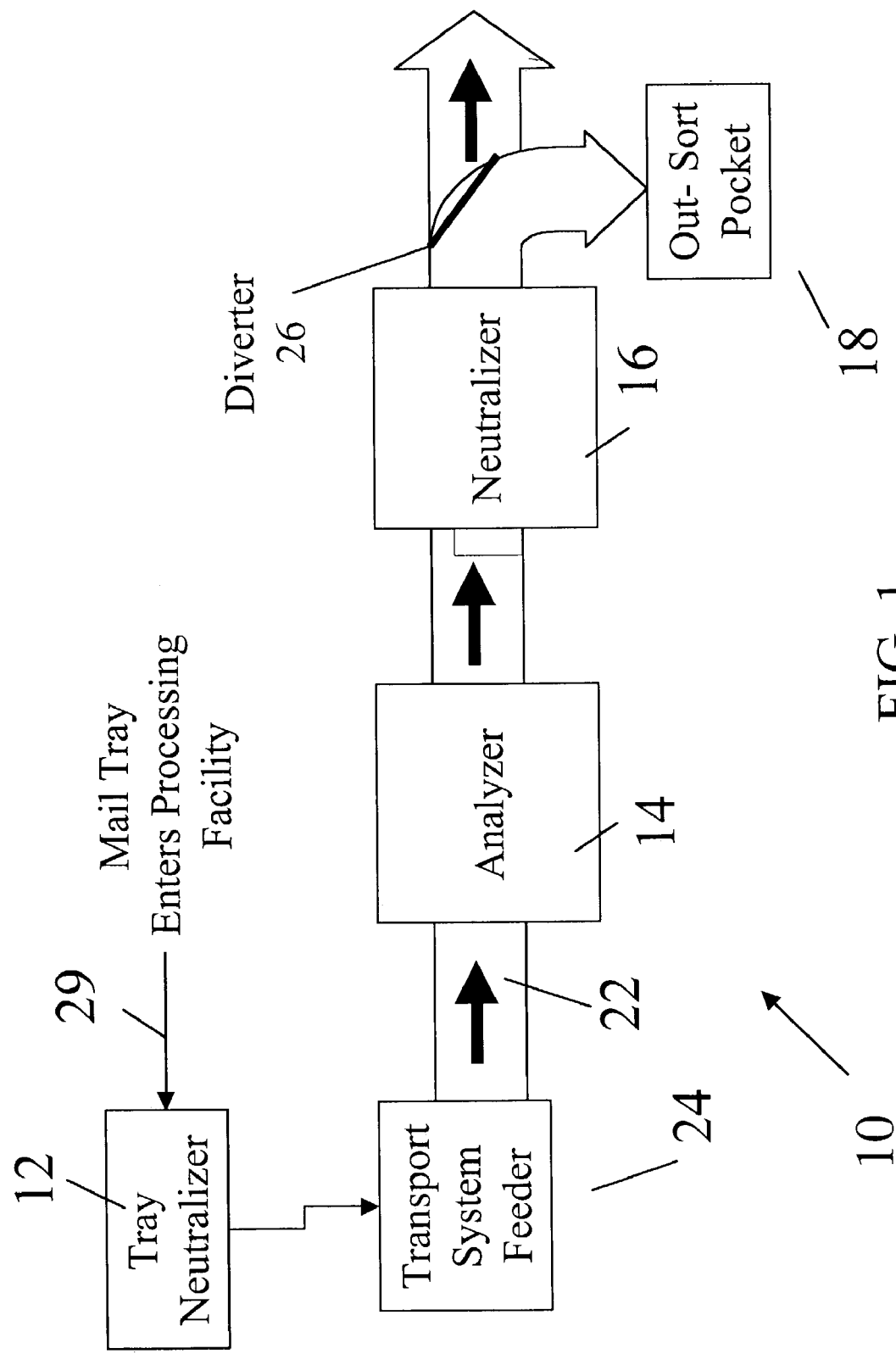
FIG. 1 is a schematic representation (block diagram) of the present invention.

Referring to FIG. 1, the system of the present invention includes a mail tray initial neutralizing sub-system 12, a subsequent neutralizing sub-system 14, a early discrimination (potentially hazardous material detection) sub-system 16, a diverting mechanism 26, and a receiving and holding sub-system (secure out-sort pocket) 18. A feeder sub-system 24 provides the mail from trays, after initial neutralization by neutralizing sub-system 12, to the transport system 22.

Figure 2:
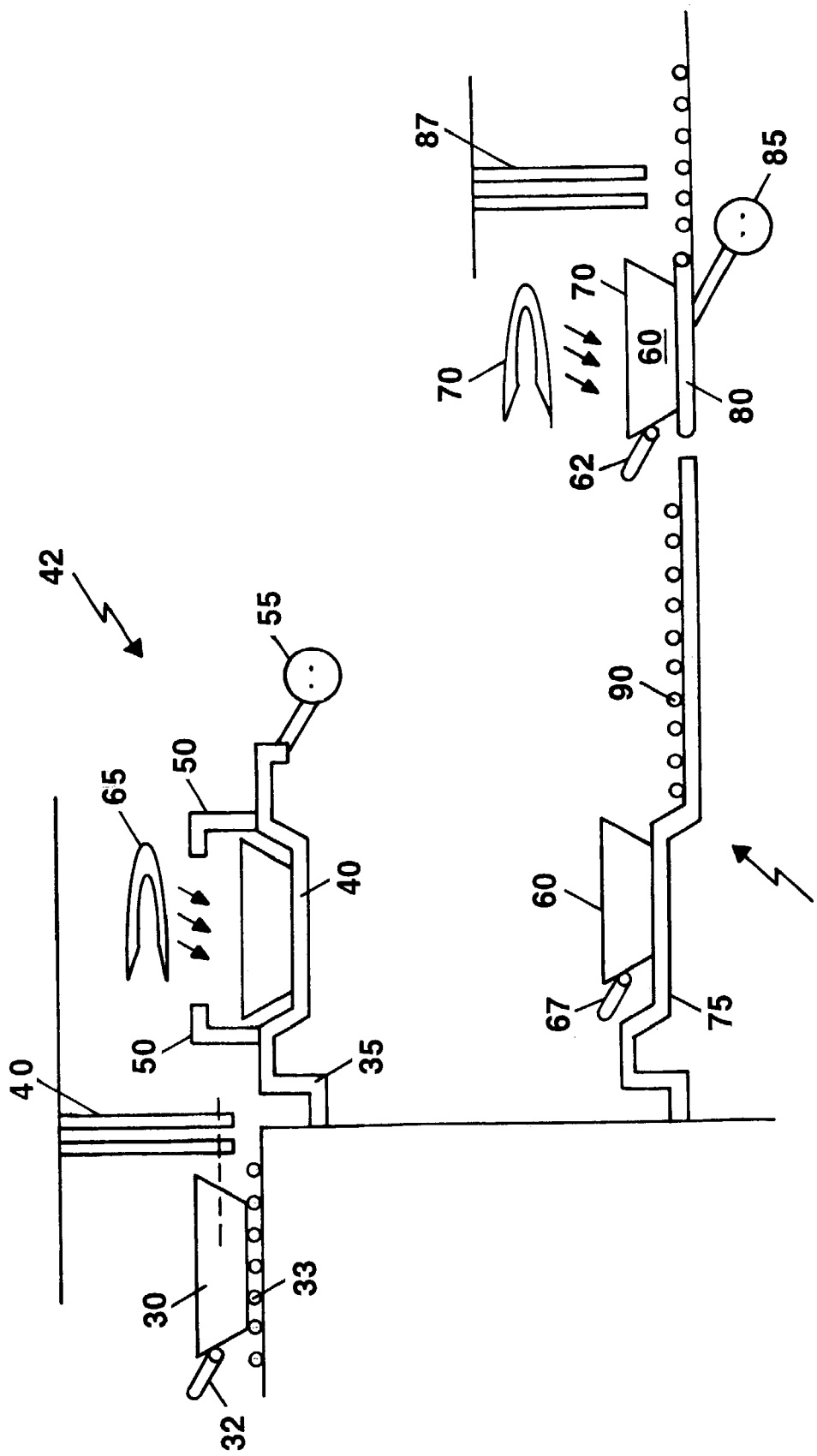
FIG. 2 is a graphical schematic representation of an embodiment of an initial neutralizing sub-system of the present invention.

An embodiment of the initial neutralizing sub-system 12 of the present invention is shown in FIG. 2. Referring to FIG. 2, a positioning mechanism 32, such as, but not limited to, a pneumatic pusher, is capable of conveying the incoming tray 30 through radiation blocking component 45. Mail items are located inside the incoming tray 30. In an alternate embodiment, intake conveyor 33 is used to transport an incoming tray 30 through radiation blocking component 45. The radiation blocking components may be, but are not limited to, radiation blocking curtains. In one embodiment, a robotic system (not shown) arranged to remove the lid of the incoming tray or otherwise uncover the tray, is located after the radiation blocking component 45. Other embodiments of means of uncovering the incoming tray 30 include mechanical uncovering systems. A structure 35 is disposed to receive the incoming tray 30. A frame 40 is connected to the structure 35 and is capable of movement with respect to the structure 35. In the embodiment of FIG. 2, the frame 40 is pivotally connected to the structure 35. (In one embodiment, the frame 40 is a section of structure 35.) The frame 40 is formed to receive and hold the incoming tray 30. The frame 40 has removable retainers 50 capable of retaining the incoming tray 30. An actuator device 55 is connected to the frame 40. In the embodiment of FIG. 2, the actuator device 55 is capable of producing both a constrained oscillation and a complete rotation. The actuator device 55 may be, but is not limited to, a motor connected to a rocker arm or a motor and eccentric rocker. A neutralizing radiation source 65 provides neutralizing radiation to the incoming tray 30.

In the embodiment shown in FIG. 2, the radiation source 65 is disposed over the frame 40 and receiving tray 60 is vertically disposed under the frame. The receiving tray 60 is capable of receiving contents of the incoming tray 30. Another structure 75 is capable of receiving and holding the receiving tray 60 and capable of constrained movement. A section 80 is pivotally connected to the remainder of the structure 75 and is formed to receive and hold the receiving tray 60. Another actuator device 85 is connected to the section 80, the actuator device 85 being capable of producing a constrained oscillation. The actuator device 85 may also be, but is not limited to, a motor connected to a rocker arm or a motor and eccentric rocker. Another neutralizing radiation source 70 provides neutralizing radiation to the receiving tray 630. In the embodiment shown in FIG. 2, the initial neutralizing sub-system 12 also includes a conveying sub-system 90 capable of conveying the receiving tray 60 away from the location underneath the first frame 40 to the location of the section 80. A positioning mechanism 67, such as, but not limited to, a pneumatic pusher, is capable of conveying the receiving tray 60 from the location underneath the first frame 40 to the conveying sub system 90. Finally, another positioning mechanism 62, such as, but not limited to, a pneumatic pusher, is capable of conveying the receiving tray 60 through another radiation blocking component 87 to a location where feeder sub-system 24 provides the mail items from the receiving tray 60 to the transport system 22. The neutralizing system 12 includes an interlock system capable of preventing operation of the radiation sources 65 and 70 if the neutralizing system 12 is open to the ambient. The neutralizing system 12 also includes filtering mechanisms capable of filtering by-products of the exposure to neutralizing radiation. (In one embodiment, shielding may also be included.)

Figure 3A:
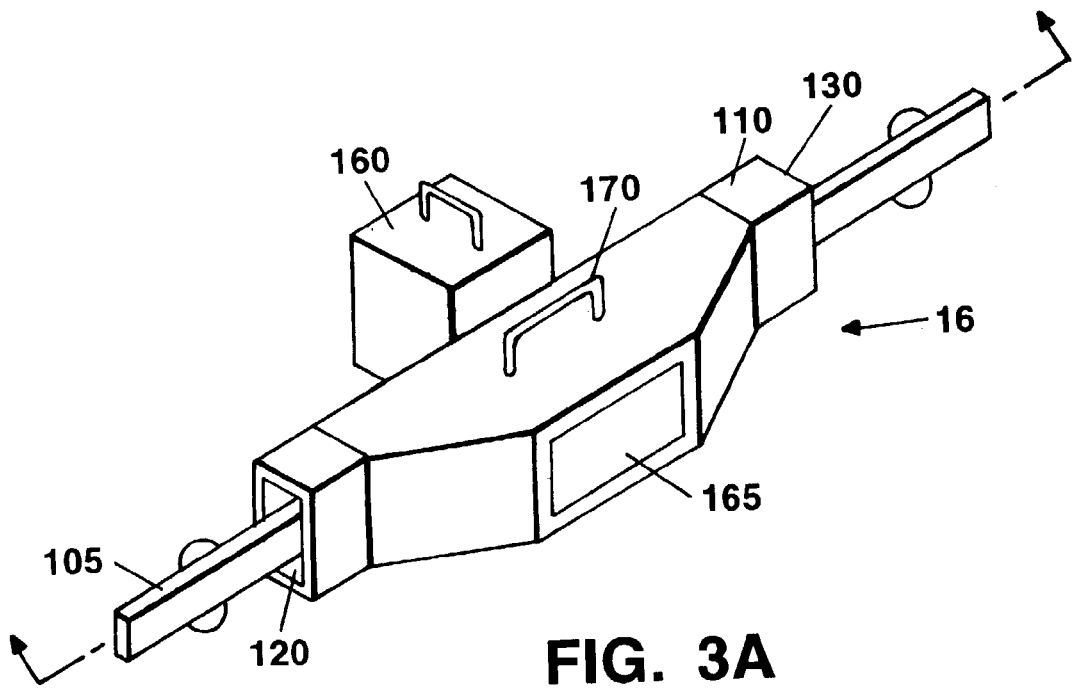
FIG. 3A depicts a graphical schematic representation of an embodiment of a subsequent neutralizing sub-system of this invention.
Figure 3B:
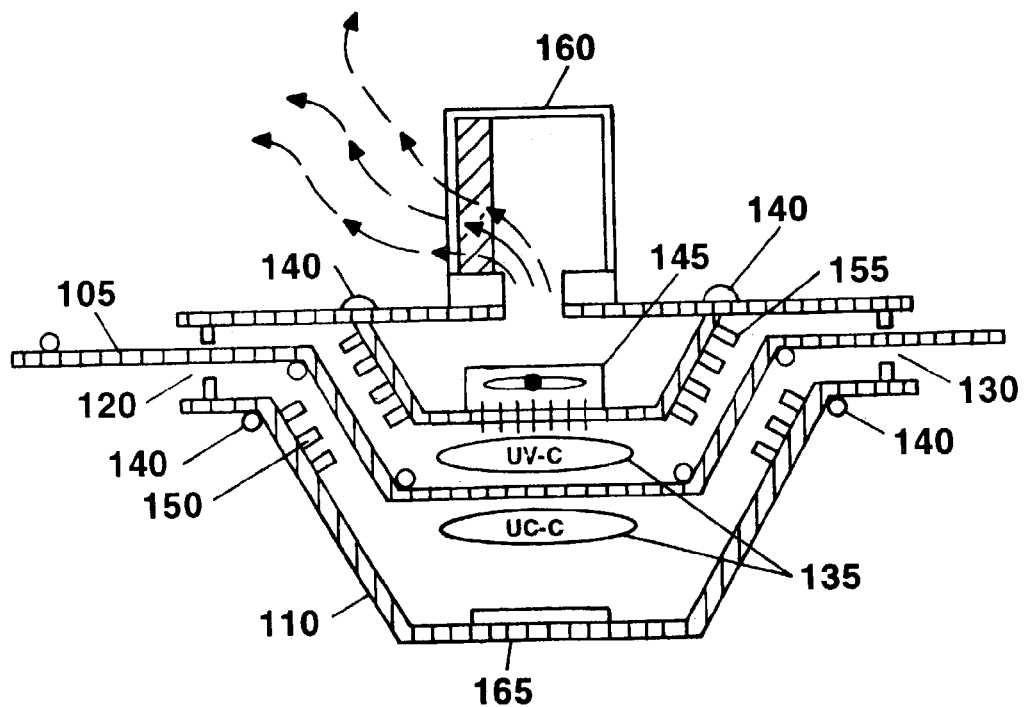
FIG. 3B depicts a graphical schematic representation of a cross sectional view of a cross section through A–A' of the subsequent neutralizing sub-system of FIG. 3A.

An embodiment of a subsequent neutralizing sub-system 14 of this invention, located on transport (conveyor) system 22, is shown in FIG. 3A. Referring to FIG. 3A, the subsequent neutralizing sub-system 14 includes a housing 170 having a first open end 120 and a second open end 130, the housing 170 extending continuously between the first open end 120 and the second open end 130. A cross sectional view of a cross section through A–A' of the subsequent neutralizing sub-system 14 of FIG. 3A is shown in FIG. 3B. Referring to FIG. 3B, a radiation sources 135, capable of producing radiation at a power level sufficient to neutralize biological agents located on the mail items, is located within the housing 170. Radiation source 135 is capable of substantially illuminating the outer surfaces of a mail item. Cooling system 145 is capable of cooling the radiation source during operation. Neutralizing sub-system 14 also includes an interlock system 140 that is capable of preventing operation of the radiation source 135 if the housing 170 is removed from the transport (conveyor) system 22. First radiation blocking component 150 and second radiation blocking component 155 are disposed in the interior of the housing 170 and are capable of preventing radiation from emanating from the first open end 120 and the second open end 130. The radiation blocking components may be, but are not limited to, radiation blocking curtains or "curtainettes". Neutralizing sub-system 14 can also include a radiation (UV filter in the embodiment in which the radiation is UV) filter window 165. In the embodiment of FIGS. 3A and 3B, the path traversed within the housing by a mail item during operation of the transport system 22 is a non-collinear path.

Figure 4A:
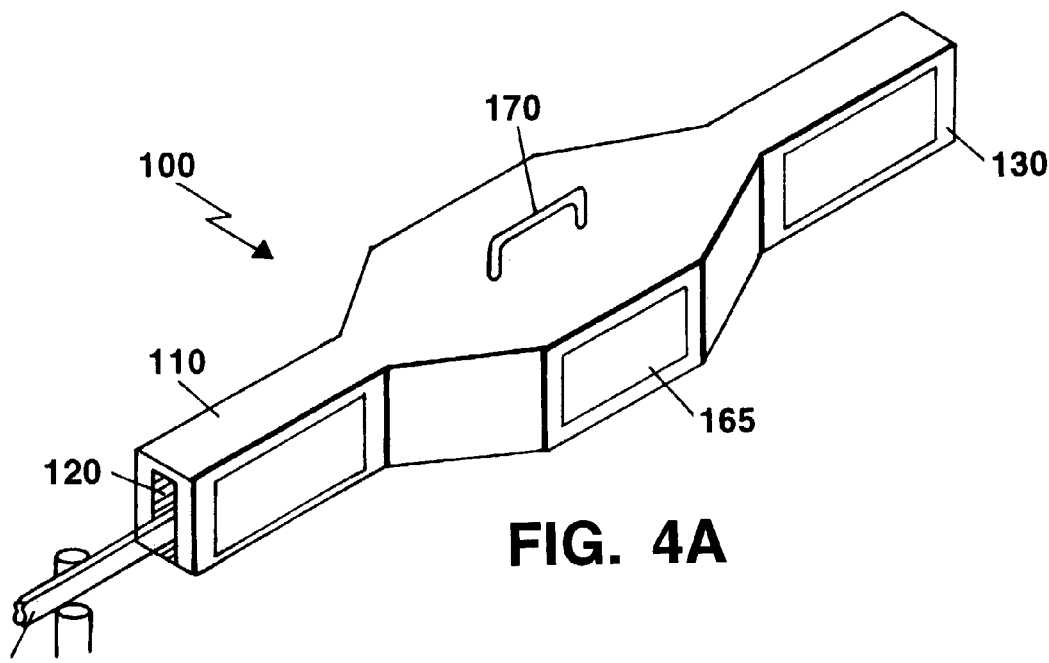
FIG. 4A depicts a graphical schematic representation of another embodiment of a subsequent neutralizing sub-system of this invention.
Figure 4B:
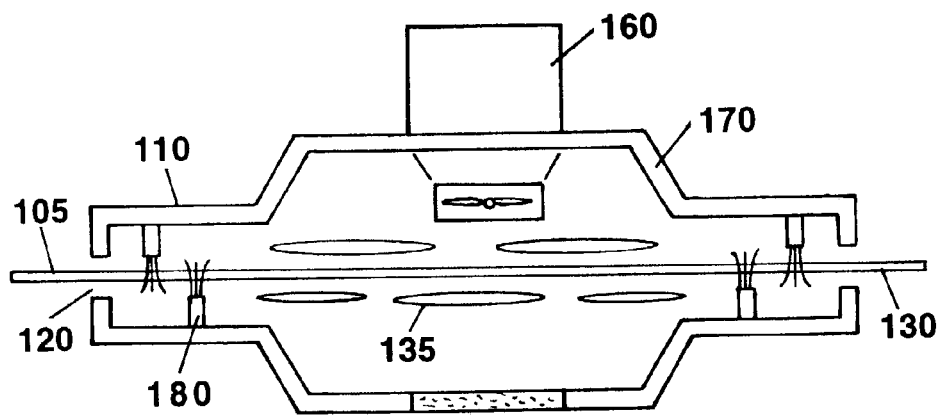
FIG. 4B is a graphical schematic representation of a cross sectional view of a cross section through B–B' of the subsequent neutralizing sub-system of FIG. 4A.
Figure 4C:
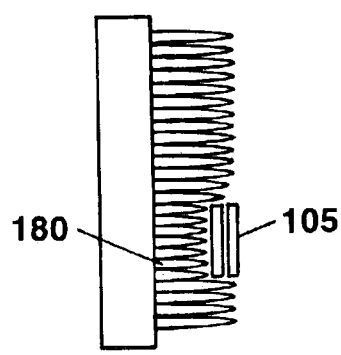
FIG. 4C is a graphical schematic representation of an embodiment of a radiation blocking component utilized in the system of FIG. 4A.

Another embodiment of the subsequent neutralizing sub-system 14 is shown in FIGS. 4A and 4B. In the embodiment shown in FIGS. 4A and 4B, the width of the housing 170 at a mid-point between the first open end 120 and the second open end 130 is larger than a first end width at the first open end 120 and is larger than a second end width at the second open end 130. In one embodiment, radiation blocking components 180 are radiation blocking curtains angled to allow the passage of transported mail items. In another embodiment, shown in FIG. 4c, radiation blocking components 180 are radiation blocking curtains or radiation blocking brushes modified to allow passage of transported mail items.

Figure 5A:
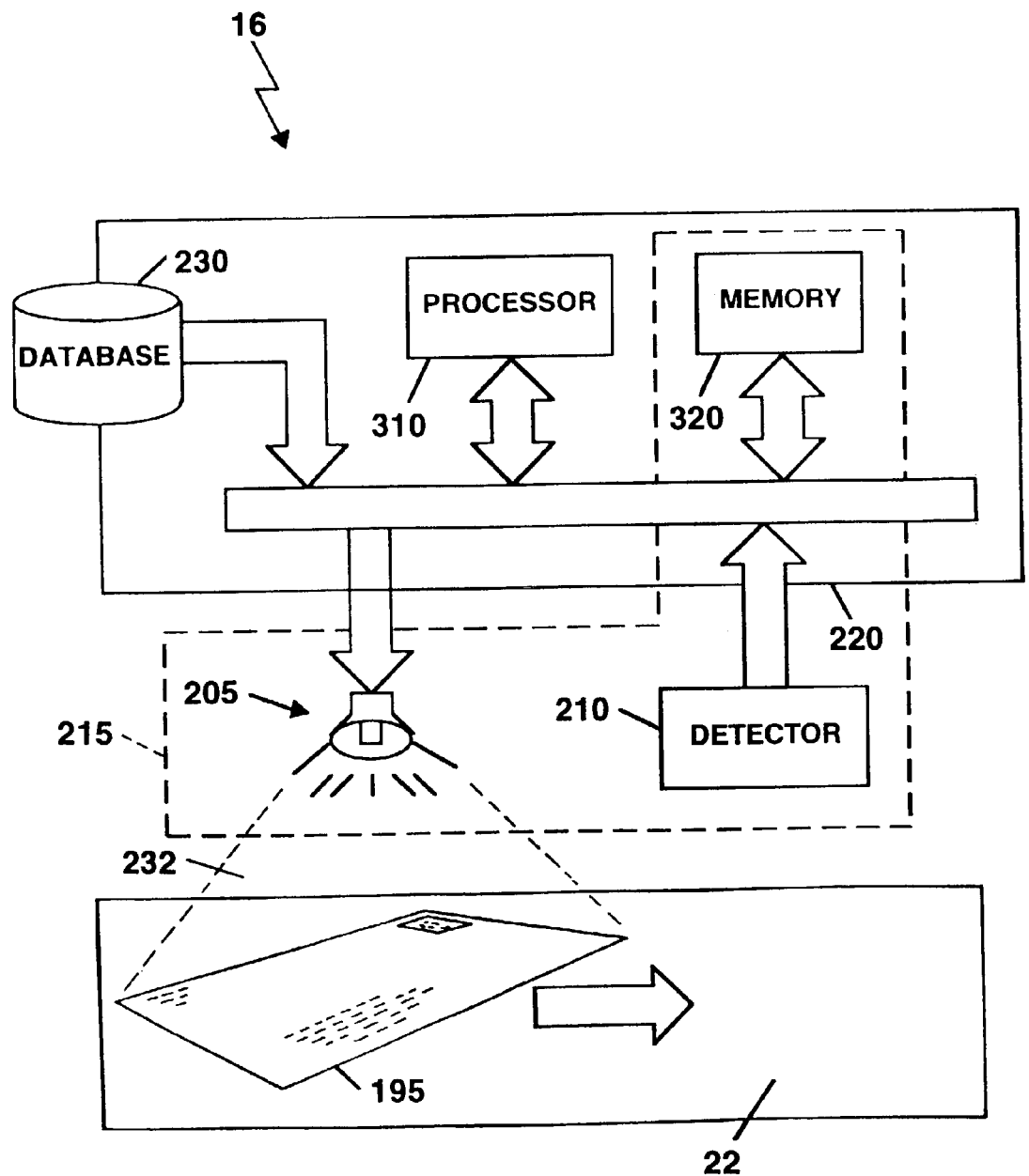
FIG. 5A is a graphical schematic representation of an embodiment of an analyzing sub-system of the present invention.

An embodiment of an analyzing sub-system 14 of the present invention is shown in FIG. 5A. Referring to FIG. 5A, the analyzing sub-system 14 includes one or more hazardous material sensors 215, a sensor including a radiation source 205, a detector 210 and an analysis algorithm in memory 320. The sensor is positioned so that, as mail item 195 is transported by transport system 22, the mail item 195 traverses the operational area 232 of the sensor 215.

Figures 5B, 5C:
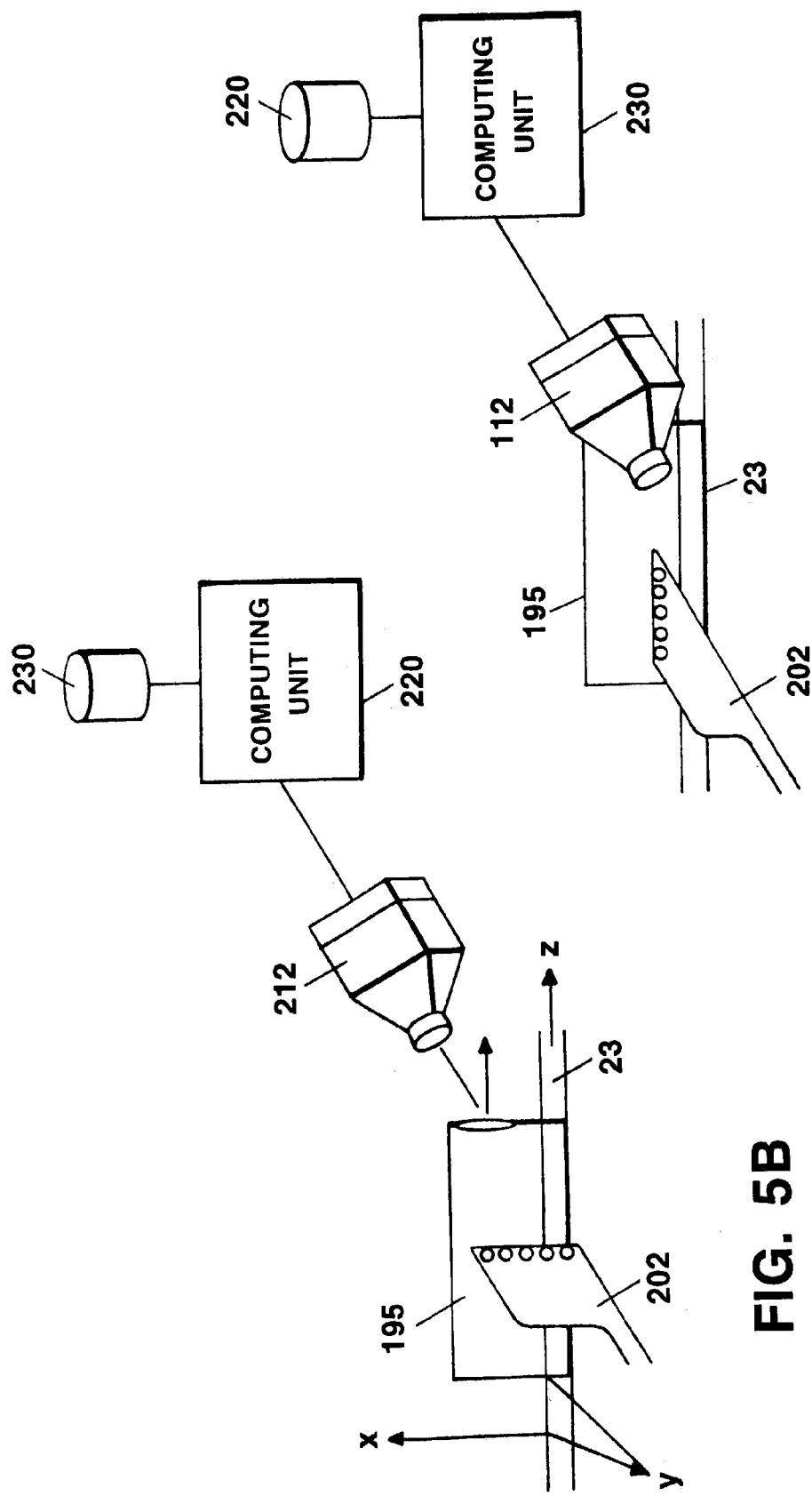
FIG. 5B is a graphical schematic representation of an embodiment of a sensor for the system of FIG. 5A.
FIG. 5C is a graphical schematic representation of another embodiment of a sensor for the system of FIG. 5A.

In one embodiment, shown in FIG. 5b, the radiation source 205 of FIG. 5a is a high brightness visible light source 207, a "stripe optical source" in one embodiment, and the detector 210 of FIG. 5a is a multi-element detector 212, such as, but not limited to, a high speed video camera or a highly sensitive multi-pixel area optical detector, such as a CCD. (A stripe source can be obtained by coupling an optical source to an optical fiber bundle and then changing the bundle configuration into a linear configuration.) The multi-element detector 212 is offset, along the direction of transport, from the radiation source 207 and on the opposite side of the mail item 195, which is being transported by "pinch belt" transport 23. (The "pinch belt" transport 23 is an embodiment of transport system 22 of FIG. 5a.) The output of the detector 212 is provided to computing unit 220. The detector output is indicative of the transmission through the mail item 195. FIG. 5c depicts another orientation of the high brightness visible light source 207 with respect to the mail item 195.

If the analyzing sub-system 14 indicates that a mail item contains potentially hazardous materials, the mail item is diverted from the transport stream of the transport system 22 by diverting mechanism 26. It should be noted that a variety of diverting mechanisms are known in the art. Exemplary diverting mechanisms are disclosed in U.S. Pat. No. 2,609,928 (issued on Sep. 9, 1952), U.S. Pat. No. 4,494,655 (issued on Jan. 2, 1985), U.S. Pat. No. 4,601,396 (issued on Jul. 22, 1986), and U.S. Pat. No. 4,627,540 (issued on Dec. 9, 1986). Although these disclosed diverting mechanisms provide practical examples of diverting mechanisms, the present invention is not limited to these.

Figure 6A:
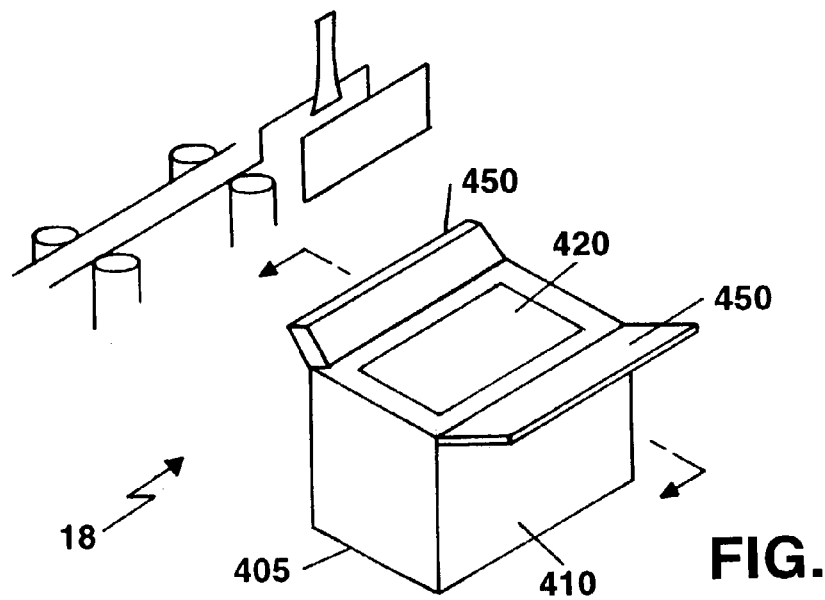
FIG. 6A is a graphical schematic representation of an embodiment of a receiving and holding sub-system of the present invention.
Figure 6B:
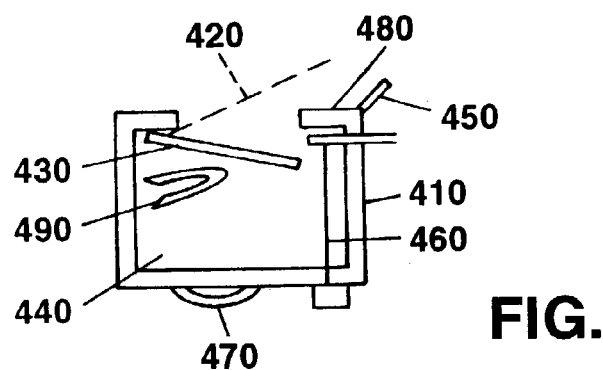
FIG. 6B is a graphical schematic representation of a cross sectional view of a cross section through C–C' of the receiving and holding sub-system of FIG. 6A.

An embodiment of the receiving and holding sub-system 18 of the present invention is shown in FIGS. 6A and 6B. Referring to FIGS. 6A and 6B, the receiving and holding sub-system (out-sort pocket) 18 includes a container 405 having an outer surface 410, an inner chamber 440, and an opening 420 in a pre-selected portion of the container, the opening 420 permitting items to pass through the outer surface 410 and enter the inner chamber 440. A cover 430 is movably disposed with respect to the opening 420. The cover enables unidirectional passage of objects from outside the container into the inner chamber 440. The cover 430 may open via an opening means such as with the weight of a piece, or by an active, triggered gate. The cover 430 may close via a closing means such as a spring load or and active closing mechanism. The cover 430 is placed in such a way that the diverting mechanism 26 can divert an item to the container 405 without disrupting item flow in the transport system 22. When closed the cover 430 effectively seals the container 405 by means of sealing component 480.

The receiving and holding sub-system 18 includes a component 450 capable of being operably connected to the transport system 22. In one embodiment, the component 450 enables attachment to new transport equipment via a standard "out-sort gate" or to existing transport equipment via an "end of machine" outlet. The component 450 may be permanently placed on the transport sub-system 22, and allows "docking" with positive rails and locks with the container 405. The receiving and holding sub-system (out-sort pocket) 18 may also include a radiation source 490 substantially located in the inner chamber 440. Locking mechanism 460 manually or automatically locks the cover 430 and disables the unidirectional passage. A handle 470 facilitates the removal and carrying of the container 405.

Figure 7:
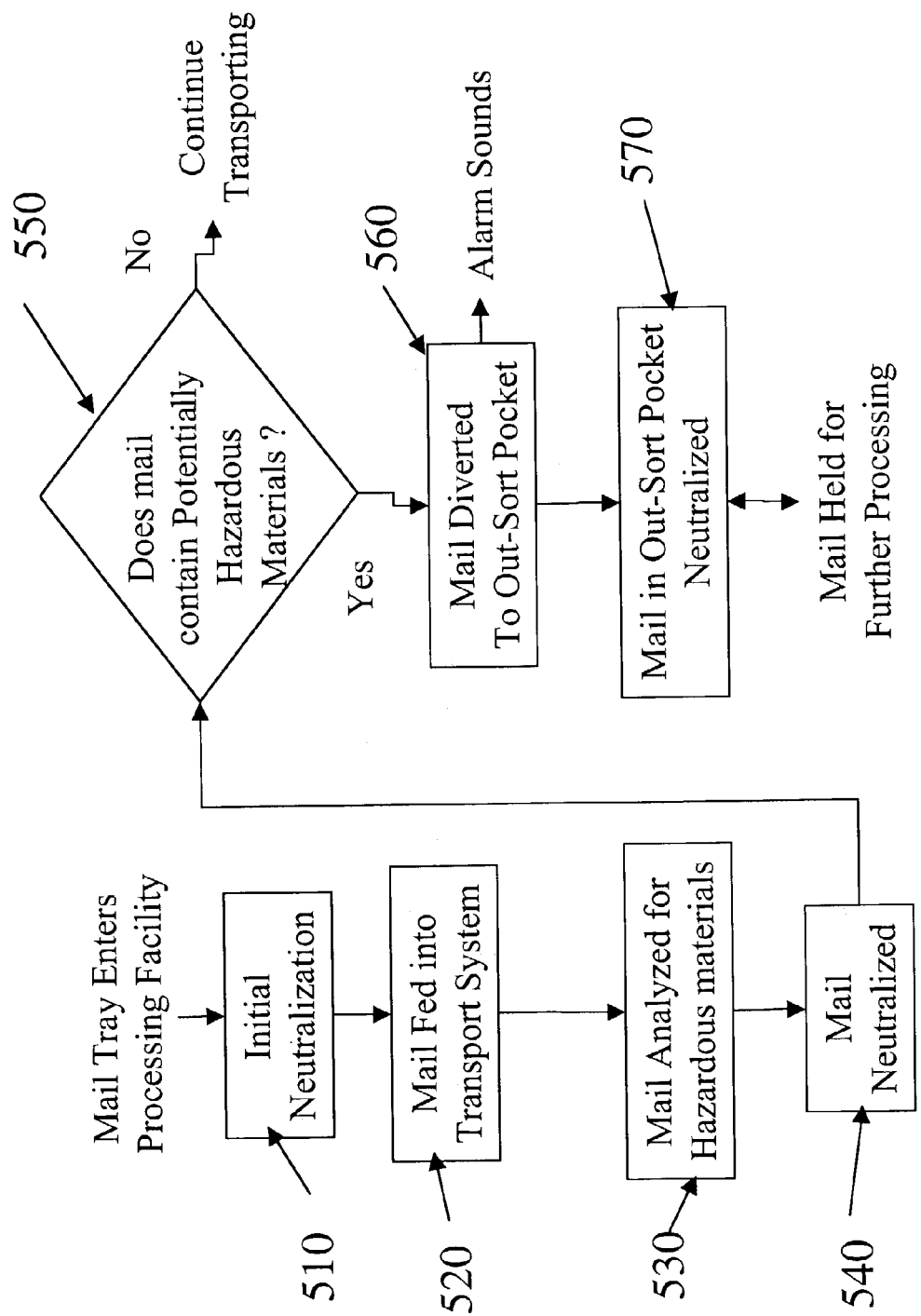
FIG. 7 is a flow chart of an embodiment of the process of the present invention.

Operation of the system is initiated by receiving an incoming tray 30 at the initial neutralizing sub-system 12, the mail items being disposed inside the incoming tray. Referring to FIG. 7, the mail items in the incoming tray 30 are neutralized to render the mail items substantially safe for handling before entering the transport sub-system 22 (step 510, FIG. 7). The neutralizing of the mail items in the incoming tray 30 is further described herein below.

Referring again to FIG. 2, the intake conveyor 33 is used to transport the incoming tray (tub) through a radiation blocking component 45 (radiation blocking curtains) into initial neutralizing sub-system 12. Structure 35 receives the incoming tray 30. Frame 40 receives the incoming tray 30. (Frame 40 may be a movable section of structure 35.) The incoming tray 30 is held on the frame 40 by retainers 50. Frame 40 is a movable frame. Actuator device 55 is operably connected to the frame 40. In one embodiment, the frame 40 is pivotally connected to the structure 35 and the actuator device 55 may be a motor connected to a rocker arm or a motor and eccentric rocker. The actuator device 55 agitates ("rocks", in one embodiment) the frame 40. Agitating the frame 40 causes the mail items inside the incoming tray 30 to move (teeter back and forth in the "rocking" embodiment) inside the incoming tray 30. As the frame 40 is being agitated, the mail items in the incoming tray 30 are being exposed to neutralizing radiation by the radiation source 65. The movement of the incoming tray 30 ensures that most of the surface of the individual mail items is exposed to the neutralizing radiation. One embodiment of the neutralizing radiation source 65 includes one or more sources of UV radiation with wavelengths in the UV-C radiation band. Another embodiment of the radiation source 65 includes one or more ionizing radiation sources (for example but not limited to Cobalt-60). The exposure time is determined by the dose (watts-sec/cm sq., for example) required to neutralize the hazardous materials and the intensity (watts/cm sq., for example) of the radiation produced by the radiation source 65. The agitating motion of the incoming tray 30 while the contents (mail items) of the incoming tray 30 are being exposed to neutralizing radiation ensures that most of the surface of the individual mail items is exposed to the neutralizing radiation. In one embodiment, after the exposure period, the removable retainers release, and the tray is transported through another radiation blocking component 87 (radiation blocking curtains) to a location where feeder sub-system 24 provides the mail items from the incoming tray 30 to the transport system 22.

Figure 8:
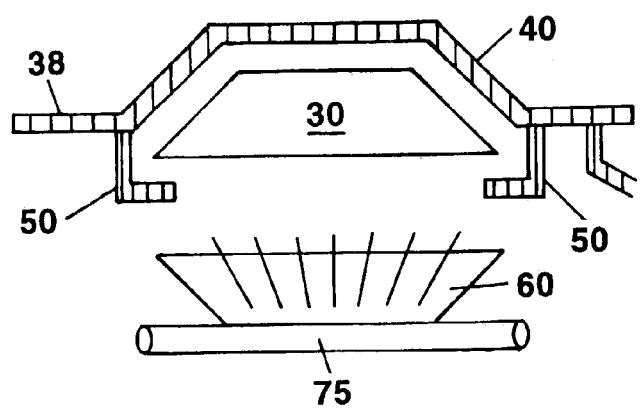
FIG. 8 is a graphical schematic representation of an embodiment of components of the sub-system of FIG. 2.

In the embodiment of FIG. 2, the incoming tray 30 is emptied onto a receiving tray 60 by overturning the incoming, tray 30. FIG. 8 depicts the overturning of the incoming tray 30 onto the receiving tray 60. Referring to FIG. 8, the frame 40 is rotated by approximately 180 degrees, overturning the incoming tray 30. Retainers 50 retain the incoming tray 30 in frame 40. The contents of the incoming tray 30 are emptied onto the receiving tray 60. The receiving tray 60 is supported by another structure 75. The structure 75 includes a section that is capable of constrained movement. Another actuator device 85 is operably connected to the structure 75. The actuator device 85 agitates ("rocks", in one embodiment) the movable section of the structure 75. As the movable section of the structure 75 is being agitated by the actuator device 85, the mail items in the receiving tray 60 are being exposed to neutralizing radiation by another radiation source 70. The exposing of the mail items in the receiving tray 60 to neutralizing radiation from radiation source 70 while being agitated by the actuator device 85 further ensures uniform neutralization of the mail items in the receiving tray 60. In one embodiment (not shown), radiation source 70 is either moved into place after contents of the incoming tray 30 are emptied onto the receiving tray 60; or, radiation source 70 is configured utilizing reflection and refraction components so that the radiation source 70 is not located under the frame 40. In the embodiment of FIG. 2, a conveying sub-system 90 conveys the receiving tray 60 away from under the frame 40.

The receiving tray 60 is conveyed to the movable section 80 of the structure 75 and is held in the movable section 80 by retaining means such as movable retainers. The exposure of the receiving tray 60 to neutralizing radiation while being subjected to agitating motion occurs at a location away from under the frame 40. Finally, positioning mechanism 62, such as, but not limited to, a pneumatic pusher, of conveys the receiving tray 60 through the radiation blocking component 87. An interlock system (not shown) prevents operation of the neutralizing system 12 if the system 12 is open to the ambient and radiation can escape. Also, radiation sources 65, 70 include appropriate cooling means and filtering of by-products of radiation exposure, For continued operation, means for removing the incoming tray 30 and providing a new receiving tray 60 have to be included in the neutralizing system 12. In one embodiment (not shown), a supply sub-system, such as, but not limited to, a pallet-like system, supplies the receiving tray 60 and a similar system is used to remove the incoming tray 30 after the contents of the incoming tray 30 have been emptied onto the receiving tray 60. In another embodiment (also not shown) similar to that of FIG. 2, the frame is rotated by a preselected angle and the removable retainers removed. The rotation of the frame allows the incoming tray 30 to gently drop and replace the receiving tray 60, after the receiving tray 60 has been conveyed away from under the frame 40. In another embodiment, the incoming tray 30 is designed to allow the incoming tray 30 to drop and be used as the receiving tray 60. It should be noted that other embodiments are possible.

The mail items in the tray emerging from initial neutralizing system 12 are provided to the feeder sub-system 24. The feeder sub-system 24 provides the mail from the tray, after initial neutralization by neutralizing sub-system 12, to the transport system 22 (step 520, FIG. 6). The feeder sub-system 24 could, in one embodiment, include manual operations since the mail items have been neutralized. In another embodiment, the feeder sub-system 24 operates without manual intervention.

The transport sub-system 22 provides the mail item to the analyzing sub-system 14. The analyzing sub-system 14 obtains an indication of whether a mail item 195 (FIG. 5A) contains potentially hazardous materials (step 530, FIG. 6). Referring to FIG. 5A, the mail item 195 is illuminated by a radiation source 205. The signal generated by the interaction between the mail item 195 and radiation from the radiation source 205 is detected by detector 210. The signal is analyzed using a computing unit 220 executing computer readable code embodied in memory 320 and compared to data from a database 230 and an early detection criterion is applied.

In the embodiment of FIGS. 5b and 5c, the radiation source 205 of FIG. 5a is a high brightness visible light source 207, a "stripe optical source" in one embodiment, and the detector 210 of FIG. 5a is a multi-element detector 212. The detector output is indicative of the transmission through the mail piece 195. "Clumps" or mounds of material will appear as reductions in transmission (or in a shadow). Since the "clumps" are small, the shadow area will be small. This relationship translates into the requirements for the detector. (A preferred detector would be a sensitive detector such as a CCD detector used for astronomy but also including high resolution.) Similarly, isolated particles translate into isolated reductions in transmission and the shadow area will be smaller than that of "clumps". "Clumps" and particles have specific shadow characteristics. For example, "clumps" have a curved shadow exhibiting a wider gray scale range transition to the background noise level (background noise as used herein refers to the signal in the absence of any other detectable features). Other detectable features, such as lettering, folds, and markings exhibit a sharper transition in gray scale to the background noise level. The brightness of the source is selected such that the difference between "clumps" or particles and other detectable features can be discerned. The output of the detector is provided to computing unit 220 where it is analyzed utilizing an algorithm residing in memory 320.

In one embodiment of the algorithm, the algorithm utilizes a conventional algorithm to obtain grayscale values and obtains "shadow" characteristics (gray scale gradients) around reductions in transmission that are potentially "clumps" or particles. The algorithm distinguishes between ordered reductions in transmission due to addresses, bar codes and the reductions in transmission due "clumps" and particles utilizing the specific shadow characteristics of the "clumps" and particles. The results of the analysis are compared to thresholds stored in memory 320 (FIG. 5a) or database 230 (in this embodiment memory 320 could perform the function of database 230). An early warning criterion is applied by comparing the results of the analysis to the thresholds. If the results of the analysis exceed the thresholds, the early warning criterion indicates that the mail piece 195 contains potentially hazardous materials. However, it should be noted that the above described method does not discriminate with respect to the nature of the material comprised in the "clumps" and particles. Any clump forming or particulate material having the same or similar shadow characteristic will be detected as being potentially hazardous materials.

In another embodiment of the analyzing sub-system, the source of radiation 205 is an illumination source in the visible range of wavelengths. The mail item 195 is conveyed by transport system 22 and moves in the direction of the arrow. It should be noted that the means for transporting the mail item 195, the transport system 22 for example, can also include means for determining the speed of transport and position along the transport path (an encoder, for example). The determination of the speed and position allows a timing signal to be generated so that illumination can be synchronized with the position of the mail item 195. The source of radiation 205 and the detector 210 include optical elements designed to enable the generation of a digital image of the mail item 195. In one embodiment, the illumination source 100 includes an unsymmetrical elliptical reflector as described in U.S. Pat. No. 5,770,841. In another embodiment, the illumination source 100 can include other optical elements so that when combined with the optical elements in the detector a desired image of the mail piece 10 is formed. Detector 210 could be, for example, a CCD detector or a CMOS detector. A digital image of the mail item 195 is obtained from the detector 210. It should be noted that the digital image could be obtained as an entire image or as a collection of line images depending on the structure of the detector used.

The digital image is then processed and the location and content of blocks containing relevant data (addresses, ZIP codes, etc.) identified (see for example U.S. Pat. No. 6,289,109). The algorithm that identifies the location containing relevant data can be, for example, the correlation and threshold algorithm disclosed in U.S. Pat. No. 5,386,482 or the algorithm for detecting Areas of Interest (AOI) found in M. Wolf et al., "Fast Address Block Location in Handwritten and Printed Mail-piece Images", Proc. Of the Fourth Intl. Conf. on Document Analysis and Recognition, vol.2, pp.753–757, Aug. 18–20, 1997, or the segmentation methods defined in P. W. Palumbo et al., "Postal Address Block Location in Real time", Computer, Vol. 25, No. 7, pp. 34–42, July 1992, or the algorithm for generating address block candidates described in U.S. Pat. No. 6,014,450. Once the block is identified. The address blocks are then classified as such (see for example, U.S. Pat. No. 6,014,450).

If the data in the blocks of interest is printed data, optical character recognition (OCR) techniques can be used to obtain the information in the blocks of interest. The identifying of the address blocks and the OCR is performed, in one embodiment, by processor 210 following instructions embodied in memory 320. The information obtained from the blocks of interest—addresses, ZIP codes, structure of the blocks, missing return address blocks, etc.—is compared against the database 230. (The information obtained from the blocks of interest could have been obtained in the normal processing of the mail and the radiation source and detector used could be those used for the electronic reading of addresses—OCR.) Database 230 contains known factors that would render a mail piece suspicious. Based on those factors—known suspicious names and addresses, known targeted addressees, known suspicious ZIP codes, structure of the blocks, missing return address blocks—a score or probability of suspiciousness is generated. An early warning criterion is applied by comparing the score to a threshold. If that score or probability exceeds the threshold, the early warning criterion indicates that the mail piece 195 is suspicious and may contain hazardous materials.

If a longer transport path and/or physical buffers are present in the transport sub-system 22, or if the time to analyze is increased or other techniques improve the analysis time required, other sources, such as X-rays, laser sources, and detection techniques, such as handwriting analysis, techniques for detecting hazardous materials, may be utilized. Sample possible analysis, sources and techniques are shown, but not limited to, in Table 1 below.

TABLE 1

| Radiation Source | Interaction | Analysis Form | Data that indicates presence of potentially hazardous materials | Early Warning Criterion |
|---|---|---|---|---|
| Visible or IR | Reflection | location and content of blocks containing relevant data (addresses, ZIP codes, etc.) | known suspicious addresses, known suspicious ZIP codes, structure of the blocks, missing return address blocks | Score based on closeness to Suspicious data |
| Visible or IR | Reflection | location and content of blocks containing relevant data (addresses, ZIP codes, etc.) and hand written data | In addition to the above, information relating to the structure of the handwriting-loopiness, openness, self correlation or coordinate information and writing pressure information | Score based on similarity with Suspicious data |
| Visible or IR | Reflection | Reconstruction of a three dimensional image from the two dimensional image produced by the detector | Known suspicious "mounds" or protrusions | Score based on similarity with Suspicious data |
| source of coherent radiation | absorption of the coherent radiation induces emission of radiation by components of the mail piece | emission spectrum for the detected emitted radiation | known emission spectra for suspicious substances | Score based on similarity with Suspicious data (at peak, observed spectrum within Threshold of known spectrum) |
| (source of coherent radiation or broadband continuum light source) and means 104 for changing or selecting the | absorption of the coherent radiation induces emission of radiation by components of the mail piece | emission spectrum, synchronizing the scanning of the emitted radiation wavelength with the scanning of the coherent radiation source wavelength | known emission spectra for suspicious substances | Score based on similarity with Suspicious data or threshold for differences at suspicious spectrum peaks |

TABLE 1-continued

| Radiation Source | Interaction | Analysis Form | Data that indicates presence of potentially hazardous materials | Early Warning Criterion |
|---|---|---|---|---|
| wavelength of the radiation source scanning X-ray source | X-ray detector such as photo-multiplier tube (PMT) | histogram of pixel intensities produced by back scattered radiation | histogram of pixel intensities produced by low atomic number (low Z) elements such as found in explosives | departure from "normal" histogram above a given Threshold |
| source of low intensity radio waves-a train of pulses of predetermined pulse width and radio wave frequency | Excite Nuclear Quadrupole Resonance (NQR) | a spectrum, intensity as a function of frequency | known NQR spectra for suspicious substances | threshold for differences at suspicious spectrum peaks |
| a source or an array of sources of thermal neutrons | Emission of gamma rays of predetermined frequencies | Detected emission at the predetermined frequencies | known response for nitrogen | If output at the known suspicious frequencies exceeds a threshold, a score is generated |
| a source of X rays (including extended sources for computed tomography) | absorption of X-rays by the mail piece | structure of objects located inside of the mail piece | structure of known suspicious objects | If the detected structure is within a given threshold of the known suspicious structure, a score is generated |
| A high brightness light source | Formation of shadows (reduction in transmission) | Determination of the shadow or transmission characteristics | Known shadow characteristics for "clumps" and particles | Score based on similarity to Known shadow characteristics for "clumps" and particles |
| a source of ultrasound radiation | scattering and transmission of ultrasound from the mail piece | structure of objects located inside of the mail piece | structure of known suspicious objects | If the detected structure is within a given threshold of the known suspicious structure, a score is generated |

Figure 9:
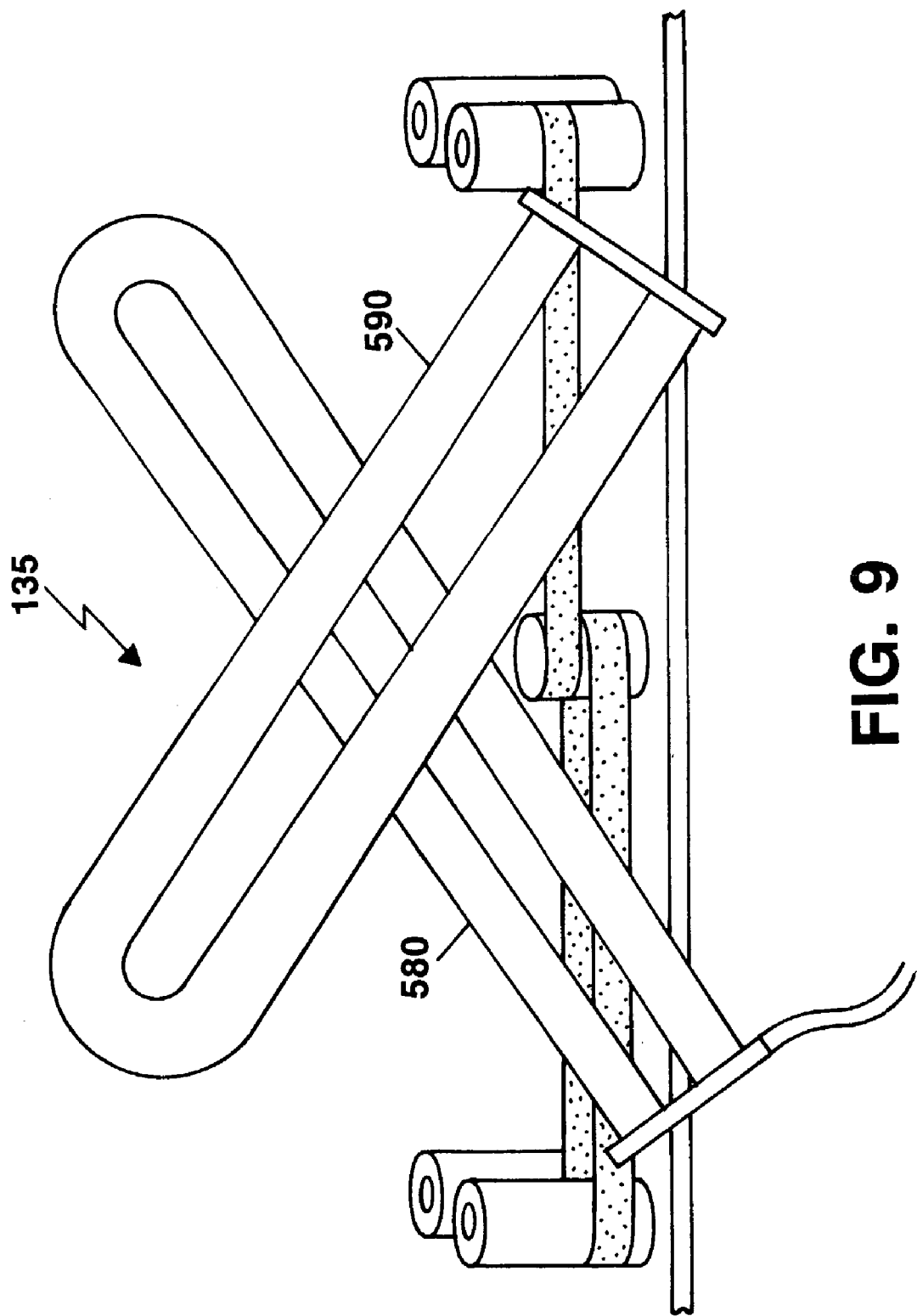
FIG. 9 is a graphical schematic representation of an embodiment of the radiation source in the sub-system of FIGS. 3B and 4B; and, FIG. 10 is a schematic representation (block diagram) illustrating the interrelation between the sub-systems of this invention.

The transport sub-system 22 provides a mail item from the analyzing sub-system 14 to the neutralizer 16 in order to expose the outer surfaces of the mail item (step 540, FIG. 6) to neutralizing radiation. Neutralizing the outer surfaces of the mail item will render the mail item substantially safe for handling and will also substantially neutralize any hazardous material released during transport. The time of exposure and the intensity of the neutralizing radiation are selected so that a neutralizing dose is delivered. If the neutralizing radiation can penetrate through the surface of the mail item (for example, in the embodiment in which the source of neutralizing radiation is an ionizing radiation source such as, but not limited to, Cobalt 60), the neutralizing radiation can also neutralize hazardous materials inside the mail item. Referring again to FIGS. 3a, 3B, 4A, 4B, the mail item is transported under the housing 110. The housing includes a neutralizing radiation source 135 capable of substantially illuminating the outer surfaces of the mail item. An embodiment of the neutralizing radiation source 135 is shown in FIG. 9. By placing radiation source 580 and 590 at an angle, a mail item of a predetermined height can be exposed. In the embodiment in which the cooling system 145 involves air removal, the removal of air from the enclosed housing may create a condition in which hazardous materials released during transport outside the neutralizer 16 are substantially drawn into the neutralizer 16.

If the analyzing sub-system 14 indicates that a mail item contains potentially hazardous materials (step 550, FIG. 7), the mail item is diverted from the transport stream by the diverting mechanism 26. Since during transport, hazardous material can emanate from mail items, mail items both in front and behind an item indicated as contains potentially hazardous materials may also be, in one embodiment, indicated as carrying potentially hazardous materials. In one embodiment, a number of mail items in front and behind the item indicated as contains potentially hazardous materials are diverted to the receiving and holding sub-system (secure out-sort pocket) 18.

The diverted mail item is isolated in the receiving and holding sub-system (secure out-sort pocket) 18. The diverted mail item is inserted into the out-sort pocket 18 through a cover 430 (FIG. 6B) enabling unidirectional passage of mail items into the out-sort pocket 18. Am alarm signal can be generated when a mail tem is inserted in the out-sort pocket 18. If the receiving and holding sub-system (secure out-sort pocket) 18 includes a radiation source 490 (FIG. 6B), the diverted mail items can be further neutralized (step 570, FIG. 7). Neutralizing the diverted mail item inside the out-sort pocket 18 can neutralize hazardous materials released during transport to the out-sort pocket 18 and substantially prevent a plume of hazardous material from emanating from the out-sort pocket 18 when a subsequent item is inserted. The out-sort pocket 18 can be removed from the transport sub-system 22. Upon removal, the locking mechanism 460 (FIG. 6B) will lock the cover 430.

Figure 10:
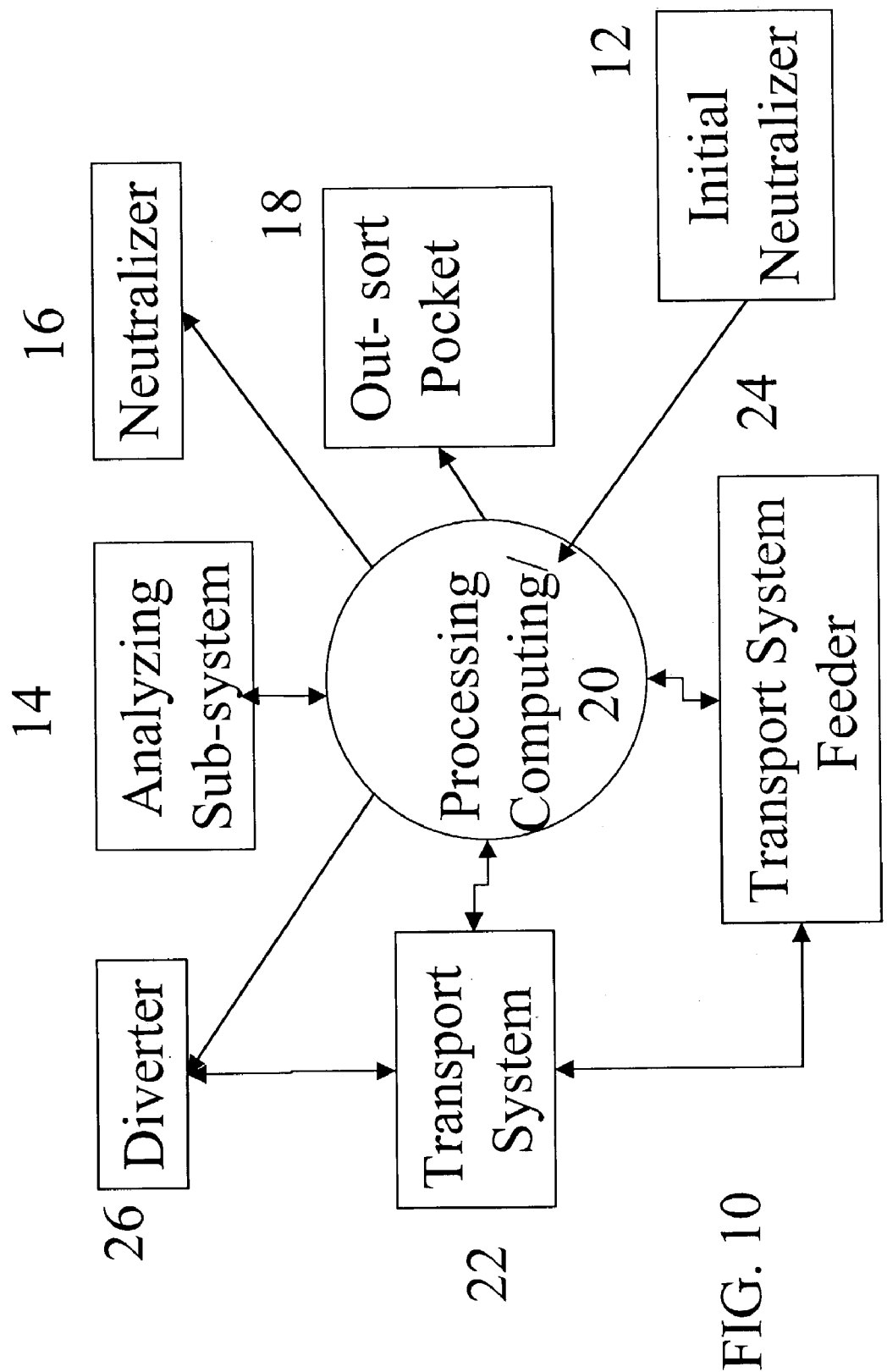

Control of the agitating motion, release of the removable retainers 50, control of the conveyors 33 and 90 and of the radiation sources 65 and 70 in the initial neutralizing sub-system 12, control of the radiation sources 135 in the neutralizing sub-system 16, timing of the radiation source 205,generation of an alarm signal, the analysis of detector data, the generation of an indication of the presence of hazardous materials in the analyzing sub-system 14, and the communication of the indication of the presence of hazardous materials in a given mail piece are examples of functions that may be performed by a processing/computing sub-system 20. The above list of functions is exemplary and is not deemed or meant to be exhaustive. The processing/computing sub-system 20 (FIG. 10) may be, in one embodiment, distributed, including many processors located at each sub-system. In another embodiment, the processing/computing sub-system 20 may be centralized or may be a hybrid system, partially centralized and partially distributed. FIG. 10 illustrates the interaction between the sub-systems 12, 22,24, 14, and 16 and the processing/computing sub-system 20.

The sub-systems of this invention are easily retrofitted into existing mail transport and sorting systems. The neutralizing sub-system 16 and the analyzing sub-system 14 can be integrated into an existing mail transport (conveyor) system 22 or designed into a future one. Initial neutralizing sub-system 12 is placed at the initial point of a mail transport (conveyor) system 22, thereby enabling retrofit or design into a future system.

The embodiments described above have been described with respect to a mail item. "Mail Item", as used herein, refers to any addressed object in a package or mail delivery system or any item being delivered by means of a mass distribution system.

As used herein, the term "neutralizing" refers to deactivating, degrading, rendering substantially harmless, decontaminating, and/or sterilizing any hazardous agent detected. For example, if a bio-hazard, such as anthrax, is detected, "neutralizing" means treating it so that it is not a substantial, or any, risk to people, such as by subjecting the anthrax to UV-C radiation or ionizing radiation (such as, but not limited to, Cobalt-60).

As used herein, the term "neutralizing radiation source" refers to a radiation source utilized to neutralize mail items, to a radiation source utilized to neutralize the mail and to by-products of utilizing the radiation source if the by-products also assist in neutralizing the mail items, and also to other neutralizing sources such as, but not limited to, chlorine dioxide or ozone.

Although the system of this invention is described herein above with the three in-line sub-systems, initial neutralizing sub-system 12, a subsequent neutralizing sub-system 16, an analyzing sub-system 14, and one off-line sub-system, receiving and holding sub-system (secure out-sort pocket) 18, it should be noted that alternative embodiments of the system 10 can be configured with more components or fewer components depending on system specifications. In one embodiment, a number of subsequent neutralizing sub-system 16 are placed along the transport path of the transport system 22 in order to render both the mail items and sections of the path substantially neutralized. The operation of the system of this invention is described herein above with one order of operations, it should be noted that the order of operation of the analyzing sub-system 14 and the neutralizing sub-system 16 can be interchanged without affecting the benefits of this invention. Therefore, the number of components shown and the order of the operations should not be considered a limitation to this invention.

An alternative application of this invention could include the neutralization of many common bacteria, viruses and molds to prevent the spread of diseases via the mail.

Although the invention has been described with respect to various embodiments, it should be realized this invention is also capable of a wide variety of further and other embodiments within the spirit and scope of the present invention.

What is claimed is:

1. A method for rendering mail items safe for handling, the method comprising the steps of:
   neutralizing the mail items to render the mail items substantially safe for handling before entering a transport sub-system;
   providing the mail items to the transport sub-system;
   exposing outer surfaces of at least one of the mail items to neutralizing radiation while the at least one of the mail items is being transported by the transport sub-system;
   analyzing the at least one of the mail items;
   the analyzing comprising:
      illuminating the at least one of the mail items with a light source;
      detecting light transmitted through the at least one of the mail items;
   diverting the at least one of the mail items based on said analysis.

2. The method of claim 1 wherein the step of neutralizing the mail items comprises the steps of:
   receiving an incoming tray having the mail items disposed therein;
   exposing the mail items in the incoming tray to neutralizing radiation while agitating the incoming tray.

3. The method of claim 2 wherein the step of neutralizing the mail items further comprises the steps of:
   emptying the incoming tray onto a receiving tray;
   exposing the mail items in the receiving tray to neutralizing radiation while agitating the receiving tray.

4. The method of claim 1 wherein the step of exposing the outer surfaces of the at least one of the mail items comprises the steps of:
   exposing the outer surfaces of the at least one of the mail items to neutralizing radiation while the at least one of the mail items is being transported under a housing to substantially avoid escape of neutralizing radiation.

5. The method of claim 4 wherein the step of exposing the outer surfaces of the at least one of the mail items further comprises the step of:
   removing by-products of the exposure to the neutralizing radiation.

6. The method of claim 1 wherein the step of analyzing the mail items comprises the steps of:
   transporting the at least one of the mail items through an operational area;
   sensing the presence of a potentially hazardous material in the at least one of the mail items.

7. The method of claim 1 further comprising the step of:
   receiving and holding the diverted at least one of the mail items.

8. The method of claim 7 wherein the step of receiving and holding said diverted one of the mail items further comprises the steps of:
   isolating the diverted at least one of the mail items.

9. The method of claim 7 wherein the step of receiving and holding said diverted one of the mail items further comprises the steps of:
   neutralizing the diverted at least one of the mail items.

10. A system for rendering mail items safe for handling, the system comprising:
   a neutralizing sub-system capable of rendering the mail items substantially neutralized and safe for handling before entering a transport sub-system;
   a neutralizing sub-system capable of exposing outer surfaces of at least one of mail items to neutralizing radiation while the mail items are being transported by the transport sub-system;
   an analyzing sub-system capable of obtaining, while the mail items are being transported by the transport sub-system, an indication of whether the at least one of the mail items contains potentially hazardous materials;
   said analyzing sub-system comprising:

a light source operatively positioned to illuminate the mail items while being transported; and a detector capable of detecting light transmitted through the mail items;

a diverting mechanism capable of diverting mail items.

11. The system of claim 10 further comprising:

a receiving and holding sub system capable of receiving the diverted mail items.

12. The system of claim 10 further comprising:

a processing and computing sub-system.

13. The system of claim 10 wherein the analyzing sub-system further comprises:

at least one processor receiving and processing data from said detector.

14. The system of claim 10 wherein the neutralizing sub-system capable of substantially neutralizing mail items before entering a transport sub-system further comprises:

a structure capable of receiving an incoming tray and having a movable section;

an actuator device operably connected to the structure; and, a neutralizing radiation source in operational relationship to the incoming tray.

15. The system of claim 10 wherein the neutralizing sub-system capable of neutralizing outer surfaces of at least one of mail items further comprises:

a housing having a first open end, a second open end;

at least one radiation source substantially located within said housing and capable of substantially illuminating the outer surfaces of the at least one mail item;

an interlock system capable of preventing operation of the at least one radiation source under preselected conditions.

16. An neutralizing system for rendering mail pieces substantially safe for handling, the neutralizing system comprising:

a structure capable of receiving an incoming tray and capable of movement;

said structure comprising a frame, said frame being capable of receiving and holding the incoming tray and capable of movement with respect to another section of said structure; an actuator device operably connected to the frame; and, a neutralizing radiation source in operational relationship to the incoming tray.

17. The neutralizing system of claim 16 wherein the frame includes removable retainers capable of retaining the incoming tray.

18. The neutralizing system of claim 16 further comprising:

a receiving tray capable of receiving contents of the incoming tray;

another structure capable of receiving and holding the receiving tray and capable of constrained movement;

another actuator device operably connected to the another structure; and another neutralizing radiation source in operational relationship to the receiving tray.

19. The system of claim 18 further comprising:

a conveying sub system capable of conveying the receiving tray away from the frame.

20. A neutralizing system for exposing outer surfaces of at least one mail item while the at least one mail item is being transported by a transport system, the neutralizing system comprising:

a housing having a first open end, a second open end;

at least one radiation source substantially located within said housing and capable of substantially illuminating the outer surfaces of the at least one mail item;

a first radiation blocking component disposed in the interior of said housing, in proximity to the first open end and substantially across a transport path; said first radiation blocking component being capable of preventing radiation from emanating from the first open end;

a second radiation blocking component disposed in the interior of said housing, in proximity to the second open end and substantially across a transport path; said second radiation blocking component being capable of radiation from emanating from the second open end;

an interlock system capable of preventing operation of the at least one radiation source under preselected conditions.

21. The system of claim 20 further comprising:

a filtering sub-system capable of removing by-products produced by the at least one radiation source.

22. The system of claim 20 wherein a path traversed by the at least one mail item within the housing while being transported by the transport system constitutes a non-collinear path.

23. The system of claim 20 wherein a mid-width at a mid-point between the first open end and the second open end is larger than a first end width at the first open end and is larger than a second end width at the second open end.

24. A method for rendering mail pieces substantially safe for handling, the method comprising the steps of:

receiving an incoming tray having the mail items disposed therein;

transporting the incoming tray though a radiation blocking component;

exposing the mail items in the incoming tray, after transporting though a radiation blocking component, to neutralizing radiation while agitating the incoming tray.

25. The method of claim 23 further comprising the steps of:

emptying the incoming tray onto a receiving tray;

exposing the mail items in the receiving tray to neutralizing radiation while agitating the receiving tray.

26. A method for exposing outer surfaces of the at least one mail item, the method comprising the steps of:

exposing the outer surfaces of the at least one mail item to neutralizing radiation while the at least one mail item is being transported under a housing to substantially avoid escape of neutralizing radiation;

providing radiation blocking components located substantially across a path of transport under the housing; and substantially blocking escape of radiation from inlet and outlet sides of the housing.

* * * * *

UNITED STATES PATENT AND TRADEMARK OFFICE
CERTIFICATE OF CORRECTION

PATENT NO. : 7,247,865 B2 Page 1 of 1
APPLICATION NO. : 10/335501
DATED : July 24, 2007
INVENTOR(S) : Juan E. Flores et al.

It is certified that error appears in the above-identified patent and that said Letters Patent is hereby corrected as shown below:

In column 16, line 18, 'being capable of' should read -- being capable of preventing --

In column 16, line 39, "though a radiation" should read -- through a radiation --

In column 16, line 42, "though a radiation" should read -- through a radiation --

In column 16, line 44, "claim 23" should read -- claim 24 --

Signed and Sealed this

Eighteenth Day of September, 2007

JON W. DUDAS
*Director of the United States Patent and Trademark Office*